United States Patent [19]
Dahmen et al.

[11] Patent Number: 5,985,797
[45] Date of Patent: Nov. 16, 1999

[54] HERBICIDAL COMPOSITIONS BASED ON N-ISOPROPYL-N-(4-FLUOROPHENYL) (5-TRIFLUOROMETHYL-1,3,4-THIADIAZOL-2-YLOXY)ACETAMIDE

[75] Inventors: Peter Dahmen, Neuss; Dieter Feucht, Monheim, both of Germany

[73] Assignee: Bayer Aktiengesellschaft, Leverkusen, Germany

[21] Appl. No.: 09/085,881

[22] Filed: May 27, 1998

Related U.S. Application Data

[63] Continuation-in-part of application No. 08/889,992, Jul. 10, 1997, abandoned.

[30] Foreign Application Priority Data

Jul. 17, 1996 [DE] Germany .......................... 196 28 777

[51] Int. Cl.⁶ .......................... A01N 43/36; A01N 43/40; A01N 43/50

[52] U.S. Cl. .......................... 504/130; 504/138; 504/139

[58] Field of Search .................................... 504/130, 138, 504/139

[56] References Cited

U.S. PATENT DOCUMENTS 4,130,413  12/1978  Handte et al. .............................. 71/90

FOREIGN PATENT DOCUMENTS

| 1 236 106 | 5/1988 | Canada . |
| 0 248 968 | 12/1987 | European Pat. Off. . |
| 26 40 730 | 3/1978 | Germany . |

*Primary Examiner*—Allen J. Robinson
*Attorney, Agent, or Firm*—Sprung Kramer Schaefer & Briscoe

[57] ABSTRACT

The present invention relates to novel synergistic herbicidal combinations of N-isopropyl-N-(4-fluorophenyl)(5-trifluoromethyl-1,3,4-thiadiazol-2-yloxy)acetamide with fenoxaprop-ethyl and/or clodinafop-propargyl.

4 Claims, No Drawings

HERBICIDAL COMPOSITIONS BASED ON N-ISOPROPYL-N-(4-FLUOROPHENYL) (5-TRIFLUOROMETHYL-1,3,4-THIADIAZOL-2-YLOXY)ACETAMIDE

This is a CIP of application Ser. No. 08/889,992, filed Jul. 10, 1997, now abandoned.

The invention relates to novel synergistic herbicidal combinations of a known hetaryloxyacetamide with other known herbicides belonging to other classes which can be used particularly advantageously for selective weed control in a variety of crop plants.

The patents listed below describe hetaryloxyacetamides which are particularly active against monocotyledonous weeds (=grass weeds), but additionally also act against some dicotyledonous weeds. They are virtually exclusively soil-acting and have little foliar activity, and some of them are very selective in mono- and dicotyledonous crop plants such as cereals, maize, rice, soybeans and cotton [cf. for example EP-A 5 501 (=U.S. Pat. No. 4,509,971 and U.S. Pat. No. 4,833,243); EP-A 18 497 (=U.S. Pat. No. 4,645,525 and U.S. Pat. No. 4,756,741); EP-A 29 171 (=U.S. Pat. No. 4,408,055); EP-A 94 514 (=U.S. Pat. No. 585,471); EP-A 100 044 (=U.S. Pat. No. 4,549,899); EP-A 100 045 (=U.S. Pat. No. 4,540,430); EP-A 161 602 (=U.S. Pat. No. 4,784,682); EP-A 195 237 (=U.S. Pat. No. 4,788,291); DE-A 3 724 467; EP-A 348 734 (=U.S. Pat. No. 4,988,380); EP-A 348 737 (=U.S. Pat. Nos. 4,968,342 and 5,090,991); DE-A 4 113 421 and DE-A 4 137 827; and also WO 91/06544].

In addition, DE 4 223 465 describes synergistic mixtures of hetaryloxyacetamides with N-phenylureas, N-benzothiazolylureas, 2,6-dinitroanilines, s-triazines, as-triazinones, sulfonylureas, imidazolinones, pyridinecarboxamides and diphenyl ethers. However, none of the mixtures described therein has as yet achieved any practical significance. A disadvantage of the mixtures described in DE 4 223 465 is that their action is not always distinct in case of strong overgrowth by a variety of weeds.

It is an object of the present invention to provide on the basis of N-isopropyl-N-(4-fluorophenyl)(5-trifluoromethyl-1,3,4-thiadiazol-2-yloxy)acetamide of the formula (I)

(I)

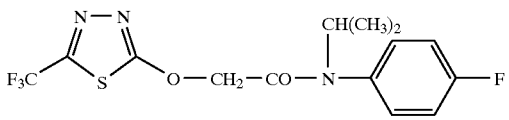

novel synergistic herbicidal mixtures which are superior in their activity to prior art mixtures and additionally act against a broad spectrum of weeds.

This object is achieved by combinations of known herbicides with the active compound of the formula (I) surprisingly found, in biological tests, to show pronounced synergistic effects with regard to activity against weeds and to be especially advantageously useful as effective broad range combination products for the selective control of weeds—both of monocotyledonous and of dicotyledonous weeds by the pre-emergence and post-emergence method—in monocotyledonous and dicotyledonous crop plants, such as, for example, maize, wheat, barley, rice, soybeans and sunflowers, allowing the effective control of a number of economically important (problem) weeds and grass weeds.

The present invention accordingly provides synergistic herbicidal compositions, characterized in that they comprise an effective amount of an active compound combination of N-isopropyl-N-(4-fluorophenyl)(5-trifluoromethyl-1,3,4-thiadiazol-2-yloxy)acetamide of the formula (I)

(I)

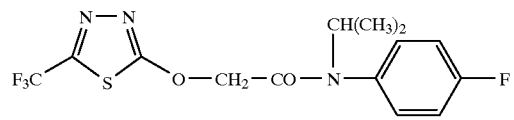

and at least one herbicidally active compound of the formula (II) or (III) (a)

(II)

a)

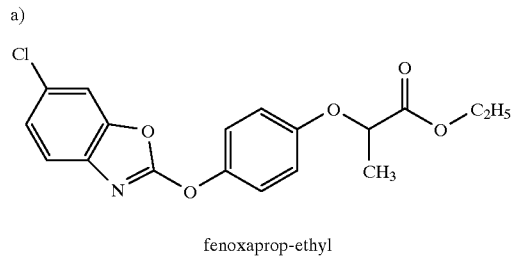

fenoxaprop-ethyl and/or
(b)

(III)

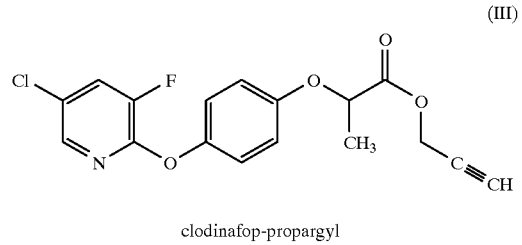

clodinafop-propargyl

The compound of the formula (I) is known from EP-A 348 737 and U.S. Pat. No. 4,968,342.

Fenoxaprop-ethyl is ethyl 2-[4-(6-chlorobenzoxazol-2-yl)oxyphenoxy]propionate, described in DE 2 640 730.

Clodinafop-propargyl is propinyl (R)-2-[4-[(5-chloro-3-fluoropyridin-2-yl)-oxy]phenoxy]propionate, disclosed in EP-A 248 968.

Hetaryloxyacetamides including the active compound of the formula (I) are particularly active against monocotyledonous weeds (=grass weeds), but additionally also act against some dicotyledonous weeds.

The active compounds (II) and (III) mentioned can be used for the selective control of a broad spectrum of grass weeds in economically important crop plants such as, for example, cereals, maize, soybeans, cotton, beet and rice. However, their activity against certain harmful monocotyledons is not always satisfactory. Important problem weeds, such as, for example, Apera spica-venti, are often not sufficiently controlled.

Surprisingly, it has now been found that the active compound combinations of the hetaryloxyacetamide of the formula (I) and the active compounds (II) and/or (III) defined above have a particularly high activity and can be used selectively in many crop plants.

Surprisingly, the herbicidal activity of the active compound combinations according to the invention is considerably higher than the sum of the activities of the individual active compounds.

This means that not merely a complementation of action is present, but a true synergistic effect, which was unforeseeable. The novel active compound combinations are well tolerated by many crop plants, and even weeds which are otherwise difficult to control, such as Apera spica-venti, are controlled well by the novel active compound combinations. The novel active compound combinations are therefore a useful addition to the range of the selective herbicides.

The active compound combinations according to the invention can be used for example in connection with the following plants:

Dicotyledonous crop plants of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledonous weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledonous crop plants of the genera: Oryza, Zea, Triticum, Hordeum, Avena, Secale, Sorghum, Panicum, Saccharum, Ananas, Asparagus and Allium.

However, the use of the active compound combinations according to the invention is in no way restricted to these genera, but also extends in the same manner to other plants.

The synergistic effect of the active compound combinations according to the invention is especially pronounced at specific concentration ratios. However, the weight ratios of the active compounds in the active compound combinations can be varied within relatively wide ranges. In general, 0.001 to 1000 parts by weight, preferably 0.01 to 100 parts by weight, especially preferably 0.1 to 30 parts by weight, of active compound of the formula (II) and/or (III) are used per part by weight of active compound of the formula (I).

The active compounds or active compound combinations can be converted into the customary formulations, such as solutions, emulsions, wettable powders, suspensions, powders, dusts, pastes, soluble powders, granules, suspo-emulsion concentrates, natural and synthetic materials impregnated with active compound, and microencapsulations in polymeric substances.

These formulations are produced in a known manner, for example by mixing the active compounds with extenders, that is liquid solvents and/or solid carriers, optionally with the use of surfactants, that is emulsifiers and/or dispersants and/or foam-formers.

If water is used as an extender, organic solvents can, for example, also be used as auxiliary solvents. Liquid solvents which are mainly suitable are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol as well as their ethers and esters, ketones such as acetone, methyl ethyl ketone, methyl isobutyl ketone or cyclohexanone, strongly polar solvents such as dimethylformamide and dimethyl sulphoxide, and water.

Suitable solid carriers are: for example ammonium salts and ground natural minerals such as kaolins, clays, talc, chalk, quartz, attapulgite, montmorillonite or diatomaceous earth, and ground synthetic minerals such as finely divided silica, alumina and silicates; suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks; suitable emulsifiers and/or foam formers are: for example non-ionic and anionic emulsifiers, such as polyoxyethylene fatty acid esters, polyoxyethylene fatty alcohol ethers, for example alkylaryl polyglycol ethers, alkylsulfonates, alkyl sulfates, arylsulfonates and protein hydrolyzates; suitable dispersants are: for example lignin-sulphite waste liquors and methylcellulose.

Adhesives such as carboxymethylcellulose and natural and synthetic polymers in the form of powders, granules or latices such as gum arabic, polyvinyl alcohol and polyvinyl acetate, or else natural phospholipids such as cephalins and lecithins, and synthetic phospholipids can be used in the formulations. Further additives can be mineral and vegetable oils.

It is possible to use colorants such as inorganic pigments, for example iron oxide, titanium oxide and Prussian Blue, and organic dyestuffs such as alizarin dyestus, azo dyestuffs and metal phthalocyanine dyestuffs, and trace nutrients such as salts of iron, manganese, boron, copper, cobalt, molybdenum and zinc.

The formulations generally comprise between 0.1 and 95 percent by weight of active compound, preferably between 0.5 and 90%.

In general, the active compound combinations according to the invention are applied in the form of ready mixes. However, the active compounds in the active compound combinations can also be formulated individually and mixed upon application, that is to say applied in the form of tank mixes.

The new active compound combinations as such or in the form of their formulations can also be used as mixtures with further known herbicides, finished formulations or tank mixes again being possible. Mixtures with other known active compounds such as fungicides, insecticides, acaricides, nematicides, bird repellants, growth promoters, plant nutrients and soil conditioners, are also possible. Furthermore, it may be advantageous for specific purposes, in particular when using the post-emergence method, to incorporate mineral or vegetable oils tolerated by plants (for example "Oleo Dupont 11E", which is commercially available) or ammonium salts such as, for example, ammonium sulfate or ammonium thiocyanate, as further additives in the formulations.

The novel active compound combinations according to the invention can be used as such, in the form of their formulations or in the use forms prepared therefrom by further dilution, such as ready-to-use solutions, suspensions, emulsions, powders, pastes and granules. They are used in the customary manner, for example by watering, spraying, atomizing, dusting or spreading.

The rates of application of the active compound combinations according to the invention can be varied within a certain range; they depend, inter alia, on the weather and on the condition of the soil. In general, the rates of application are between 0.01 and 10 kg per ha, preferably between 0.03 and 5 kg per ha, in particular between 0.05 and 3.0 kg per ha.

The active compound combinations according to the invention can be applied before and after the emergence of the plants, i.e. by the pre-emergence and post-emergence method.

The good herbicidal activity of the novel active compound combinations is evident from the examples below. While the individual active compounds show weaknesses in their herbicidal activity, the combinations all exhibit very efficient control of weeds, and this control exceeds a simple sum of the activities.

In herbicides, a synergistic effect is always present when the herbicidal activity of the active compound combination exceeds that of the active compounds applied individually.

The expected activity for a given combination of two herbicides can be calculated as follows (cf. Colby, S. R.; "Calculating synergistic and antagonistic responses of herbicide combinations", Weeds 15, pages 20–22, 1967):

If $X = \%$ damage by herbicide $A$ (active compound of group 1) at the rate of application of $p$ kg/ha and $Y = \%$ damage by herbicide $B$ (active compound of group 2) at the rate of application of $q$ kg/ha and $E =$ the expected damage caused by herbicides $A$ and $B$ at a rate of application of $p$ and $q$ kg/ha, then $E = X + Y - \left(\dfrac{X \cdot Y}{100}\right)$.

If the actual damage exceeds the calculated value, the combination is super-additive with regard to its activity, i.e. it shows a synergistic effect.

The examples below reveal that the herbicidal activity of the active compound combinations according to the invention found exceeds the calculated value, i.e. that the novel active compound combinations have a synergistic action.

USE EXAMPLES

To prepare the active compound preparations required for the tests, suitable amounts of a water-dispersible powder formulation (WP) of the hetaryloxyacetamide of the formula (I) and a commercially available formulation of the compounds (II) and/or (III), respectively, are weighed out and diluted with water to the desired concentration; by mixing, various combinations of the two active compounds were prepared.

A) Post-emergence Tests/Greenhouse

Test plants which have a height of 5 to 15 cm are sprayed with the active compound preparations in such a way as to apply the particular amounts of active compound desired per unit area. The concentration of the spray liquor is chosen such that the particular amounts of active compound desired are applied in 500 l of water per ha. After the treatment, the test plants are kept in the greenhouse under controlled conditions (temperature, atmospheric humidity, light) until the evaluation. After three weeks, the degree of damage to the plants is rated in % damage in comparison to the development of untreated control plants.

The figures denote:

0%=no action/damage (like untreated control)

100%=total destruction

Active compounds, application rates and results are listed in the tables below.

TABLE 1

Herbicidal activity of (I), clodinafop-propargyl and tank mixes of (I) and clodinafop-propargyl against *Apera spica-venti* by the post-emergence method

| Preparation | Application rate g of a.i./ha | herbicidal activity in % *Apera spica-venti* found | calc. |
|---|---|---|---|
| (I) | 60 | 40 | |
| (I) | 30 | 40 | |
| (I) | 15 | 20 | |
| Clodinafop-propargyl | 30 | 10 | |
| Clodinafop-propargyl | 15 | 0 | |
| (I) + Clodinafop-propargyl | 60 +30 | 80 | 46 |
| (I) + Clodinafop-propargyl | 30 +30 | 70 | 46 |
| (I) + Clodinafop-propargyl | 15 +30 | 50 | 28 |
| (I) + Clodinafop-propargyl | 60 +15 | 60 | 40 |
| (I) + Clodinafop-propargyl | 30 +15 | 50 | 40 |
| (I) + Clodinafop-propargyl | 15 +15 | 30 | 20 |

TABLE 2

Herbicidal activity of (I), fenoxaprop-ethyl and tank mixes of (I) and fenoxaprop-ethyl against *Apera spica-venti* by the post-emergence method

| Preparation | Application rate g of a.i./ha | herbicidal activity in % *Apera spica-venti* found | calc. |
|---|---|---|---|
| (I) | 60 | 40 | |
| Fenoxaprop-ethyl | 30 | 20 | |
| Fenoxaprop-ethyl | 15 | 0 | |
| (I) + Fenoxaprop-ethyl | 60 +30 | 60 | 52 |
| (I) + Fenoxaprop-ethyl | 60 +15 | 50 | 40 |

Notes to Tables 1 and 2:

found=activity or damage (in percent) found;

calc.=activity or damage (in percent) calculated using the COLBY formula above a.i.=active ingredient The compounds fenoxaprop-ethyl (II) and clodinafop-propargyl (III) have been used in form of the following commercially available formulations:

(II) as (R)RALON 060 EW (emulsion-in-water) (AgrEvo);

(III) as (R)TOPIK 240 EC (emulsion concentrate)(Novartis).

We claim:

1. A synergistic herbicidal composition for controlling monocotyledonous weeds comprising synergistically herbicidally effective amounts of an active compound combination of N-isopropyl-N-(4-fluorophenyl)(5-trifluoromethyl-1,3,4-thiadiazol-2-yloxy)acetamide of the formula (I)

(I)

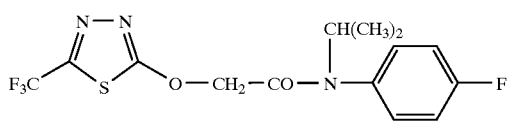

and at least one herbicidally active compound of the formula (II) or (III)

(II)

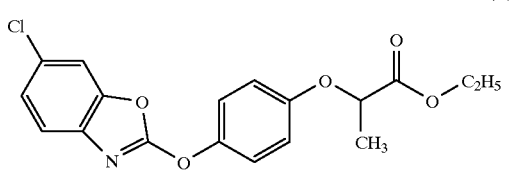

Fenoxaprop-ethyl or

-continued (III)

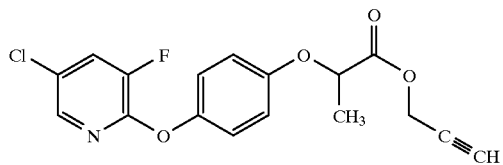

Clodinafop-propargyl wherein
0.01 to 100 parts by weight of active compound of the formula (II) or (III) are employed per part by weight of active compound of the formula (I).

2. The synergistic herbicidal composition according to claim 1, wherein 0.1 to 30 parts by weight of active compound of the formula (II) or (III) are employed per part by weight of active compound of the formula (I).

3. The herbicidal composition according to claim 1 further comprising an extender.

4. A method of controlling monocotyledonous weeds comprising administering to such weeds or to a locus from which it is desired to exclude such weeds a synergistic herbicidally effective amount of the composition according to claim 1.

* * * * *